United States Patent [19]
Cerwin et al.

[11] Patent Number: 5,788,062
[45] Date of Patent: Aug. 4, 1998

[54] SUTURE DISPENSER

[75] Inventors: Robert Cerwin, Pipersville, Pa.;
Marvin Alpern, Glen Ridge, N.J.;
Yufei Huang, Piscataway, N.J.; Emil Richard Skula, Wayne, N.J.

[73] Assignee: Ethicon, Inc., Somerville, N.J.

[21] Appl. No.: 604,200

[22] Filed: Feb. 21, 1996

Related U.S. Application Data

[63] Continuation of Ser. No. 221,678, Jun. 6, 1994, abandoned.

[51] Int. Cl.$^6$ .................................................. A61B 17/06
[52] U.S. Cl. .................................... 206/63.3; 206/380
[58] Field of Search ........................... 206/63.3, 346, 206/389, 390, 382, 383, 397, 408, 409, 480

[56] References Cited

U.S. PATENT DOCUMENTS

| | | | |
|---|---|---|---|
| 2,617,523 | 11/1952 | Zoller | 206/63.3 |
| 2,938,624 | 5/1960 | Runkel et al. | 206/63.3 |
| 3,062,372 | 11/1962 | Egler et al. | 206/63.3 |
| 3,127,992 | 4/1964 | Horine | 206/63.3 |
| 3,167,895 | 2/1965 | Egler et al. | 53/35 |
| 3,185,299 | 5/1965 | Trainer | 206/63.3 |
| 3,280,971 | 10/1966 | Regan, Jr. | 206/63.3 |
| 3,301,393 | 1/1967 | Regan, Jr. et al. | 206/56 |
| 3,444,994 | 5/1969 | Kaepernik et al. | 206/63.3 |
| 3,627,120 | 12/1971 | Bordeau | 206/63.3 X |
| 3,731,793 | 5/1973 | Hagel | 206/52 W |
| 3,876,068 | 4/1975 | Sonnino | 206/227 |
| 3,939,969 | 2/1976 | Miller et al. | 206/63.3 |
| 3,959,947 | 6/1976 | Sonnino | 53/21 FW |
| 4,142,628 | 3/1979 | Marocco et al. | 206/63.3 |
| 4,183,431 | 1/1980 | Schmidt et al. | 206/63.3 |
| 4,284,194 | 8/1981 | Flatau | 206/63.3 |
| 4,424,898 | 1/1984 | Thyen | 206/63.3 |
| 4,574,948 | 3/1986 | Huck et al. | 206/63.3 |
| 4,699,271 | 10/1987 | Lincoln et al. | 206/63.3 |
| 4,813,537 | 3/1989 | Okuhara et al. | 206/63.5 |
| 4,961,498 | 10/1990 | Kalinski et al. | 206/339 |
| 4,967,902 | 11/1990 | Sobel et al. | 206/63.3 |
| 5,228,565 | 7/1993 | Sinn | 206/63.3 |
| 5,236,082 | 8/1993 | Brown | 206/63.3 |
| 5,301,801 | 4/1994 | Sinn | 206/63.3 |
| 5,675,961 | 10/1997 | Cerwin et al. | 53/430 |

FOREIGN PATENT DOCUMENTS 662417  4/1963  Canada.

*Primary Examiner*—David T. Fidei

[57] ABSTRACT

Suture dispensers for retaining armed sutures are disclosed. The dispenser disclosed is comprised of two flat panels of material that each have a central opening. A needle park is provided so that the needle is visible in and accessible though the central openings. In preferred embodiments, the needle park is made of a thin sheet of clear material. Several alternate needle park designs are also disclosed. The two panels are preferably locked together using edge locks in the form of corresponding slits and tabs formed on the panels themselves. In addition to being inexpensive, easy to manufacture and easy to fill, the disclosed dispensers is much thinner than current designs and thus requires less storage and shipping space. Methods of loading dispensers are also disclosed. By winding the suture material in a flat spiral around a set of winding pins, the disclosed dispensers can be easily and accurately filled, yet the resulting coiled suture can be withdrawn via the central openings without twisting or kinking the suture material. In certain embodiments pressure on the central portion of the panels permits winding a spiral without the need for a central winding core. In other embodiments, pins are used to both align the panels and provide a winding guide for the suture material.

15 Claims, 9 Drawing Sheets

SUTURE DISPENSER

This is a continuation of application Ser. No. 08/221,678, filed Jun. 6, 1994, now abandoned.

The present invention relates to packaging for surgical sutures and, more specifically, relates to dispensers for packaging one or more armed sutures that are spirally wound in the dispenser and have needles positioned to be accessed through the center of the package.

BACKGROUND OF THE INVENTION

Surgeons today have a wide variety of sutures from which to choose. Both traditional materials such as gut, and newer materials such as absorbable sutures are available in a number of sizes, and a pre-cut length of suture material is typically swaged to a needle to create an armed suture. Several armed sutures are usually provided as part of a sterile package. Thus, during surgery, the sterile package is opened to expose a dispenser holding several armed sutures. It is of course necessary to retain the needles in a stable yet easily released manner so that a needle holder can be armed and provided to the surgeon. The location at which the needle is retained is generally referred to as a "needle park." The removal of the needle and use of the suture should not be impeded by the needle park and the manner in which the suture material is retained in the dispenser, nor should the dispenser permit the suture material to become twisted or kinked.

Originally, sutures were coiled and packaged in paper folders that were simply unfolded or opened to freely dispense the suture material. Such packaging, however, was difficult to fill and close. Also, paper packages did not present a good base for retaining the needle in a position where it could be easily accessed by the needle holder. Sutures packaged in paper folders also present disadvantages in handling.

Suture dispensers are known that comprise a plastic tray that forms a circular track in which the suture material is laid. A peelable foil cover overlies the tray and the needles are clipped between the sides of channels or similar structures molded into the plastic tray. An example of this type of dispenser is disclosed in U.S. Pat. No. 4,424,898—Thyen et al. A variation of this type of package is disclosed in U.S. Pat. No. 4,961,498—Kalinski et al. which discloses a two-piece plastic tray that defines an enclosed channel for retaining the suture material. A one-piece plastic tray that forms a substantially enclosed channel using a series of moveable locking flaps is disclosed in U.S. Pat. No. 4,967,902—Sobel et al. Another design of a plastic tray that provides a needle park and retains a plurality of armed sutures is disclosed in U.S. Pat. No. 5,228,565—Sinn.

However, the foregoing packages all suffer from several drawbacks, the primary being the overall expense of the package. The plastic trays found in the prior art require precision molded parts and frequently require time consuming loading methods to deposit a bundle of suture material in the outer channel. Closing the package can also be somewhat awkward, as the suture material is frequently resilient enough to spring outwardly from its coiled configuration when not restrained. Additionally, currently available plastic tray-type suture packages are bulkier than an ideal package. This bulkiness is a disadvantage because it reduces the number of dispensers that can fit into a given amount of storage space.

Thus, there exists a long-felt and unfulfilled need for a suture dispenser that is easily wound with suture material and that provides a reliable needle park that overcomes the deficiencies of both the paper folders and the plastic trays found in the prior art. Accordingly, it is an object of the present invention to provide a suture dispenser that is simple and inexpensive to manufacture and assemble. It is a further object of the present invention to provide such a package with a central opening through which the needle is accessed and the suture material dispensed. It is another object of the present invention to provide a dispenser with a needle park disposed in the vicinity of a central opening with a needle positioned so it is visible and easily accessed, preferably from either side of the package. It is still another object of the present invention to provide a dispenser that is of a minimum thickness so that the packaging density of a number of dispensers in a container is maximized.

SUMMARY OF THE INVENTION

In accordance with these and other objects of the present invention, it has now been found that an improved armed suture dispenser can be fabricated from two panels of rigid material, one of which contains the needle park. The simple yet effective design disclosed results in a dispenser that is only slightly thicker than the sum of the thicknesses of the suture material, the needle park material and the panels themselves. The panels are readily die cut from either paper products or plastic materials and are most preferably wound using a rigid winding fixture that cooperates with the panels to properly wind the suture material in a flat spiral without requiring any retaining structure incorporated into the panels themselves.

In accordance with the present invention, two separate pieces of material are brought together and the suture is coiled in a flat spiral between the sandwich. The outward spiral places each suture loop concentrically around the next. This is desirable because it prevents knotting or tangling. Additionally, the two dimensional character of the package allows for more product in less space. Finally, the central dispensing opening and needle park allow operating room personnel to see the entire needle, thereby helping to prevent inadvertent needlesticks.

Improvements in needle parks are also disclosed. Various laminations of film and other materials can be used to retain a needle using pressure. Additionally, foam, glue dots or molded portions can be adhered to the panels of the dispenser that conform to portions of the needle and act to keep the needle in place.

DETAILED DESCRIPTION OF THE PREFERRED EMBODIMENTS

Figure 1:
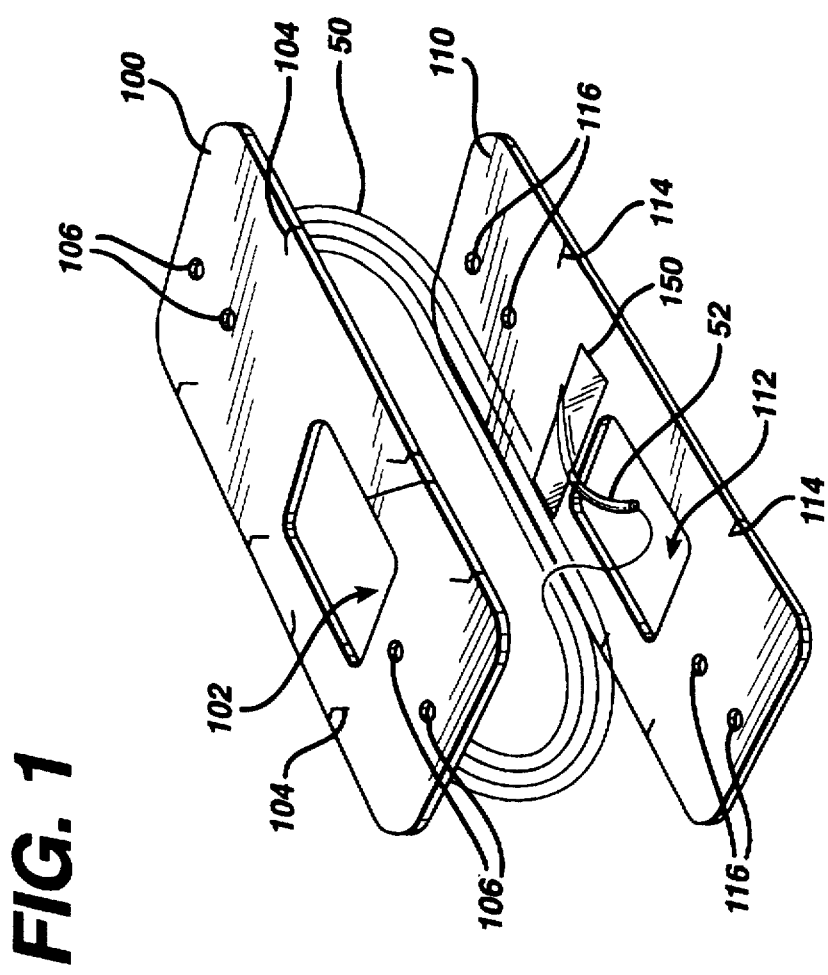
FIG. 1 is an exploded perspective view of an armed suture dispenser made in accordance with the present invention.

Referring now to FIG. 1, there is shown an exploded perspective view of a preferred embodiment of a needle dispenser made in accordance with the present invention. The dispenser is shown retaining an armed suture 50 that has a curved needle 52 affixed to its distal end. The dispenser is primarily comprised of two flat panels 100, 110. The panels 100, 110 may be made from any suitable material such as cardboard or similar paper products, or any of a number of types of plastic materials that can be made into a thin, relatively stiff sheet. Most preferably, the panels 100, 110 are flat and are manufactured by die cutting from a larger piece of stock. In accordance with preferred embodiments of the present invention, each panel 100, 110 is provided with a central opening 102, 112 that provides an access point through which the needle 52 may be loaded on to a needle holder. As explained in further detail below, the openings 102, 112 are not necessarily in registration when the panels 100, 110 are brought together to form the dispenser. One opening may be larger than the other, or may be positioned differently so that when the package is assembled, part of the surface of one of the panels 100, 110 extends across one of the openings.

Also visible in FIG. 1 are the edge locks 104, 114 that are preferably provided to retain the panels 100, 110 together to form a dispensing package. The design and implementation of the edge locks 104, 114 will be familiar to those of skill in the art. Typically, as illustrated in FIG. 1, a series of convoluted cuts 104 are made in a first panel 100 that will create a tab when displaced from the plane of the panel 100. The second panel 110 is provided with slits 114 that will be in registry with the tabs of the first panel 100 when the panels are assembled. The geometry of the tab 104 and slit 114 is chosen so that they interlock or otherwise cooperate to retain the panels 100, 110 together to form a dispenser package. It will be understood, however, that a wide variety of edge lock designs could be provided to achieve the same result, these include both other types of edge locks 104, 114 cut and folded from the material of the panels 100, 110 themselves, as well as adhesives, strips of tape, staples or other mechanical fasteners. Other alternate embodiments or equivalent edge locks in addition to molding the panels with cooperating parts that lock or snap include heat sealing or ultrasonic sealing of the edges of the panels either intermittently or continuously or using an adhesive or a cohesive applied either intermittently or continuously around the edges of the panels. Additionally, one panel can be formed with slots or similar openings that receive bendable tabs that extend from another panel made of foil or a shape retaining plastic material. In such embodiments the panels 100, 110 can also be fastened together by placing the panels in registry and punching or deforming parts of the panels. Thus, it will be understood that the term "edge locks" is meant to be defined broadly and is not limited to the tab and slit construction illustrated.

Also visible in FIG. 1 are the fixture holes 106, 116 in the panels 100, 110 that are used in certain embodiments. Upon assembly of the panels 100, 110 the fixture holes 106 in the first panel 100 are in substantial registration with the fixture holes 116 in the second panel 110. As explained in further detail below, the fixture holes 106, 116 are designed to cooperate with upstanding pins that are part of a winding fixture so that the suture material can be wound inside the dispenser. The winding fixture provides a set of rigid points over which the suture material can be wound. After the dispenser is filled, the fixture is easily withdrawn. However, the fixture holes 106, 116 are not necessary in all embodiments. In certain embodiments, pressure alone in the central portion of the panels 100, 110 will permit the winding described in detail below to be efficiently and effectively accomplished. As will be readily understood by those of ordinary skill, pressure pads can be designed that will urge the central portions of the panels 100, 110 together and sufficient force can be applied to the pads so that the suture material can be spirally wound without the need for pins or fixtures that penetrate the panels 100, 110.

Figure 1A:
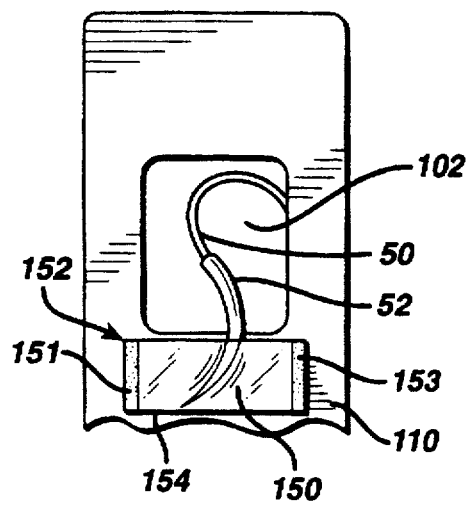
FIGS. 1A–1D are plan views, partially broken away and enlarged plan views of several embodiments of needle parks for the dispenser illustrated in FIG. 1.
Figure 1B:
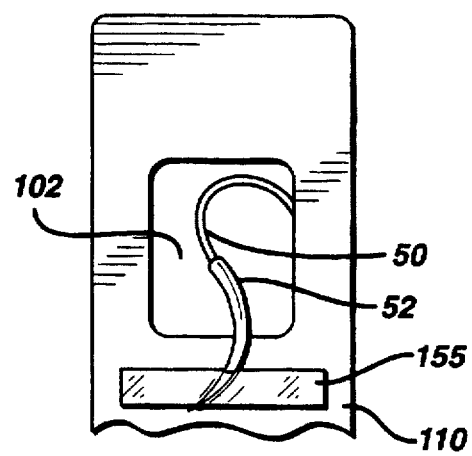
Figure 1C:
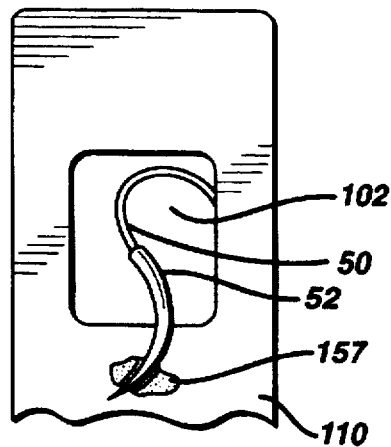
Figure 1D:
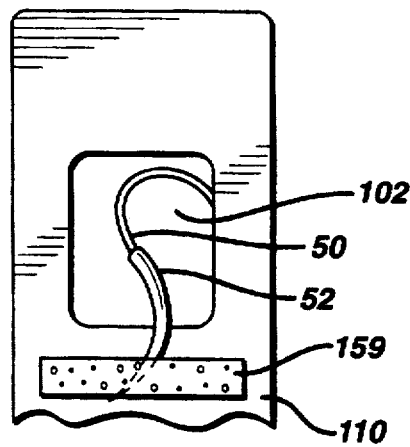

Another aspect of the present invention illustrated in FIG. 1 is the needle park 150 that retains the needle 52 in a position to be loaded into a needle holder. As illustrated, the needle 52 is most preferably disposed in a location across the central openings 102, 112 described above. The needle park 150 can be of a number of different designs. For example, a "pocket" can be created by adhering a piece of thin flexible material, such as polyethylene or a similar suitable plastic material to a surface of one of the panels 100, 110. Thus, as illustrated in FIG. 1A, a strip of material 152 may be adhered by adhesives or welding at two parallel edges 151, 153 to form the needle park 150. If desired, a third edge 154 can also be adhered to form a closed pocket. Alternatively, as illustrated in FIG. 1B, a piece of material that is coated with an adhesive, i.e., a piece of tape 155, can also function as the needle park. The tape 155 seals around the needle 52 and retains it in place. Another alternative needle park is illustrated in FIG. 1C. As shown, the needle 52 is retained by a drop of an adhesive material 157, such as hot melt glue. Although the needle 52 is firmly held in place, the bond between the smooth metal surface of the needle 52 and the hardened adhesive 157 is easily broken if the amount of adhesive is not excessive and care is taken when mounting the needle 52. Still another embodiment of a needle park is illustrated in FIG. 1D, where a strip of foam 159 is illustrated that retains the needle as shown by inserting the needle through the foam 159.

Additional needle parks useful in the present invention are illustrated in FIGS. 1E–1H.

Figure 1E:
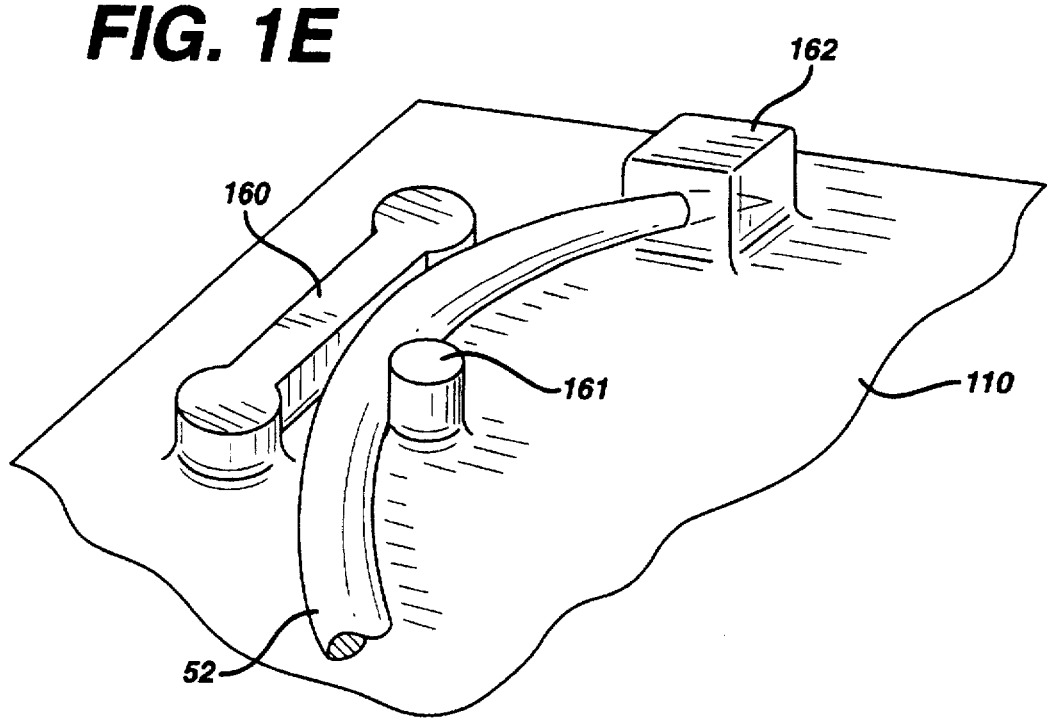
FIGS. 1E–1F are perspective views, partially broken away and enlarged, of additional embodiments of needle parks for the dispenser illustrated in FIG. 1.
Figure 1F:
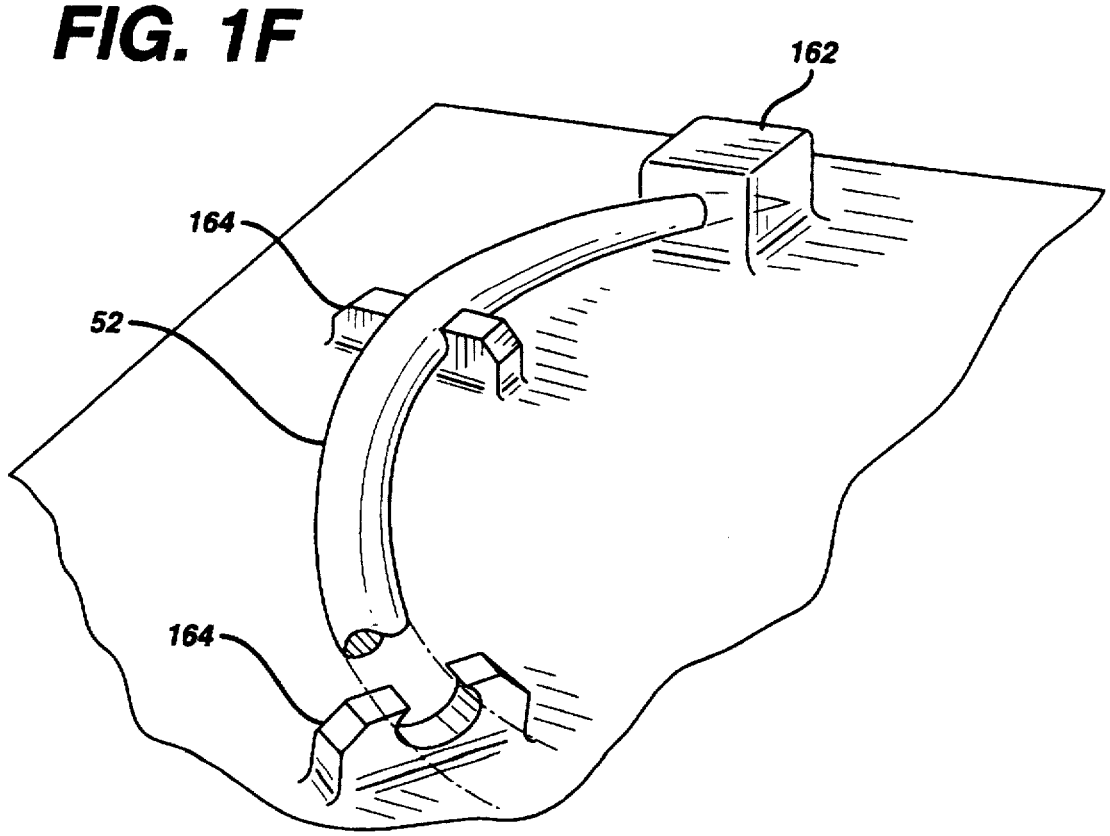

FIGS. 1E and 1F illustrate needle parks wherein small plastic portions are molded directly onto the surface of one of the panels 100, 110 using a process known as "outsert" molding. In the embodiment shown in FIG. 1E a first molded portion 160 and a second molded portion 161 cooperate to form a resilient structure that will firmly grip the needle 52 yet permit its release. Most preferable a tip block 162 is also provided to prevent the needle 52 from twisting within the package. An alternate embodiment, illustrated in FIG. 1F, uses one or more snap blocks 164 and, most preferably, also includes a tip block 162. The snap blocks are designed to accept the needle and retain it against movement during storage, but are sufficiently resilient to permit the needle 52 to be easily removed.

Figure 1G:
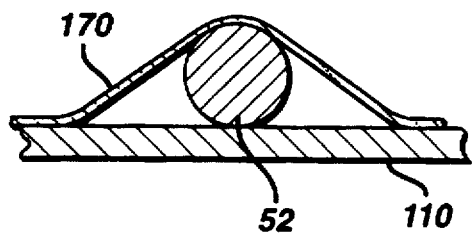
FIGS. 1G–1H are, respectively, cross-sectional and plan views of another embodiment of a needle park for the dispenser illustrated in FIG. 1.
Figure 1H:
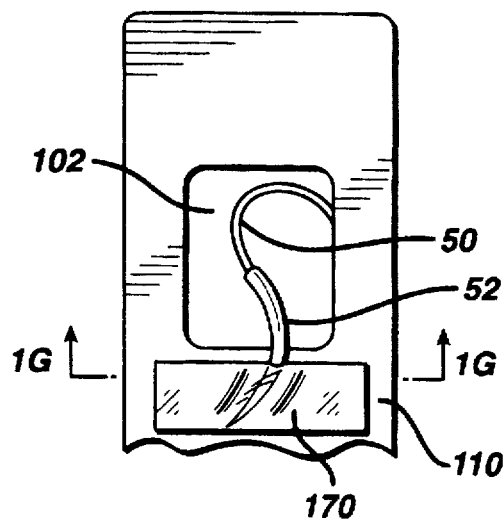

The needle park illustrated in FIGS. 1G–1H is comprised of two layers of material and is similar to that illustrated in FIGS. 1A–1B to this extent. However, this embodiment uses thermosetting plastic to form a needle park that does not conform as closely to the outer surface of the needle. As seen in cross-section in FIG. 1G, the needle 52 is sandwiched between a relatively stiff panel 110 and a layer of relatively resilient shrink wrap material 170. The application of heat causes the resilient material 170 to draw taut, but not conform to the needle 52. Thus, as seen most clearly in the cross-sectional view of FIG. 1G, the needle 52 is held between these two layers, but the top layer does not conform to a substantial portion of the needle 52, which is instead held by the compressive force generated by the tension between the two layers of material 110, 170. However, in alternate embodiments, other types of thermosetting plastic films such as "skin wrap" plastic film can be employed to produce a needle park that conforms more closely to the needle 52.

Figure 1J:
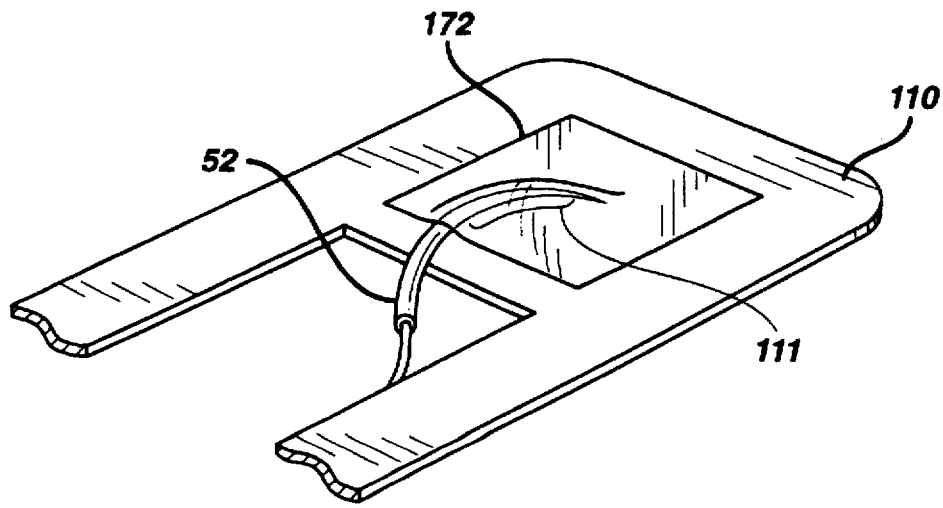
FIG. 1J is a partially broken away perspective view of an embodiment of a needle park for the dispenser illustrated in FIG. 1.

Finally referring to FIG. 1J, another alternate embodiment of a needle park is shown. In this embodiment, a clear wrap material 172 that is thermoformable is used to retain the needle. The panel 110 is provided with an access hole 111 that permits a vacuum to be drawn that will draw the material 172 into close conformance with the needle 52. After this step, the area covered by the material 172 is compressed with a hot, resilient pad that thermoforms the material 172 into a shape that will hold the needle in place. Most preferably, the vacuum is sufficient to draw some of the material 172 into the hole 111 so that a point of fixation is achieved at this location, which is most preferably located under the body of the needle 52.

In addition to the embodiments of the needle park illustrated, those of skill in the art will realize that a number of different types of tabs, slots or other features can be cut from the surfaces of the panels 100, 110 to provide a structure that retains the needle 52 or provides an adjunct to a needle park such as those made in accordance with the embodiments illustrated in FIGS. 1A–1D. In any embodiment, however, it will be appreciated that the central openings 102, 112 permit the needle 52 to be accessed from either side of the dispenser, thereby facilitating use by either left handed or right handed operating room personnel.

Figure 2A:
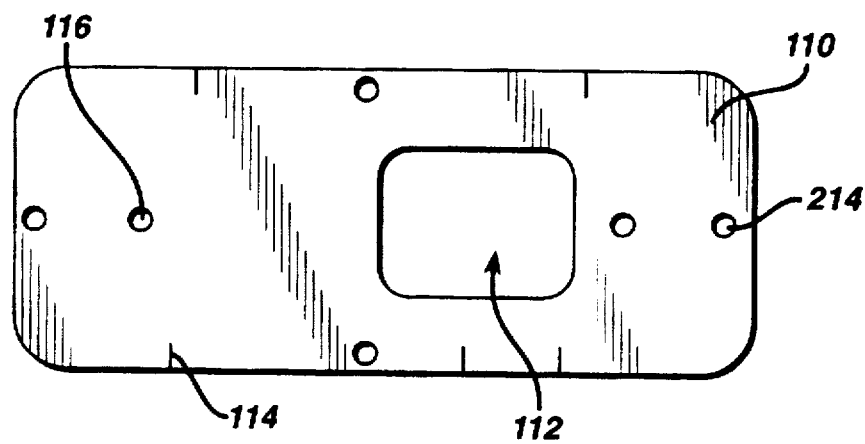
FIGS. 2A–2B are plan views of the top and bottom panel used to form the dispenser illustrated in FIG. 1.
Figure 2B:
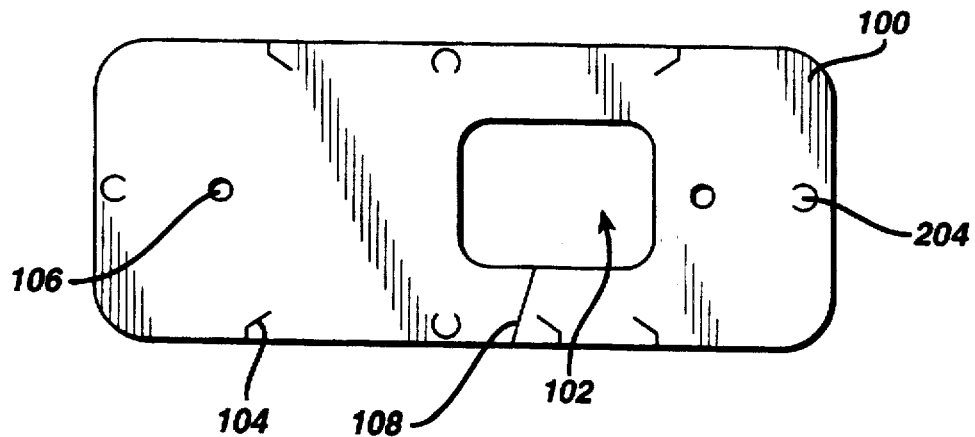

Referring now to FIGS. 2A–2B, a plan view of the panels 100, 110 of the dispenser shown in FIG. 1 are illustrated. As explained above, each panel 100, 100 is provided with a central opening 102, 112. In this view, two styles of the edge locks are illustrated. First, as described above, a set of convoluted cuts 104 form tabs that will cooperate with slits 114 to lock the longitudinal edges of the panels 100, 110. Additionally, a hole 214 and circular tab 204 is provided on each edge. These will lock the edges when the circular tabs 214 are displaced from the panel 110 and inserted into the holes 204. Also illustrated are two pairs of corresponding fixture holes 106, 116 and a slit 108 that retains the proximal end of the suture after it has been wound.

Figure 3:
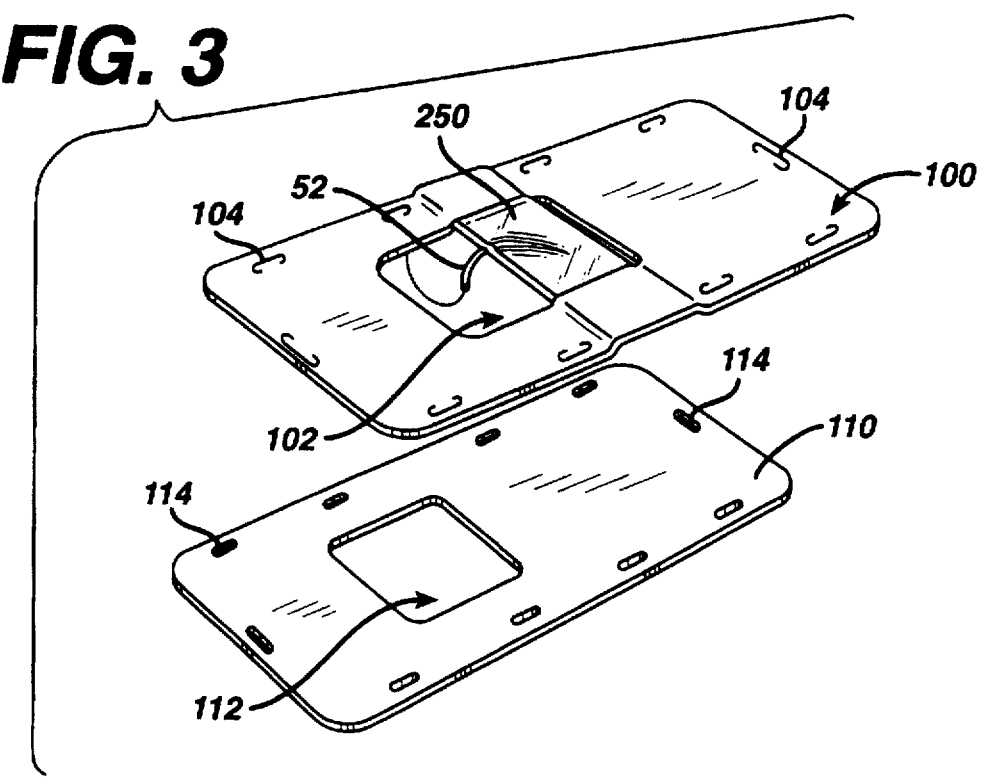
FIG. 3 is an exploded perspective view, similar to FIG. 1, of an alternate embodiment of the present invention.

An alternate embodiment of the dispenser of the present invention is illustrated in FIG. 3. In this embodiment, the needle park 250 is a "sandwich" needle park that retains the needle 52 between the two panels 100, 110, leaving a portion protruding into the central openings 102, 112. In this embodiment, the central opening 102 in the top panel 100 is larger than the central opening 112 in the lower panel 110. The material of the needle park 250 extends across the central opening 102 in the top panel 100 and upon assembly is backed by an uncut portion of the lower panel 110. The material used to form the needle park 250 in this embodiment can be coated with adhesive or cohesive on the opposing faces of the strips that are on either side of the needle 52, or can be used without an adhesive or cohesive, relying on friction to retain the needle 52. Although it is preferred that the needle park 250 be formed of a transparent plastic material, it may also be formed of a strip of foam material and the needle inserted into the foam. In other preferred embodiments, the needle park 250 can be formed from a cut and/or folded section of cardboard or other material and provide a structure for retaining the needle. Such embodiments will have a greater thickness than other embodiments, but will provide a stiffer central section, which may be necessary for some applications.

FIG. 3 also illustrates another embodiment of the edge locks 104, 114 described above. In this embodiment, C-shaped slits 104 are cut in the top panel 100 and corresponding holes 114 are cut in the lower panel 110. To lock the panels together, the cut sections of the slits 104 are displaced and inserted through the holes 114 and bent back toward their original position.

Figure 4:
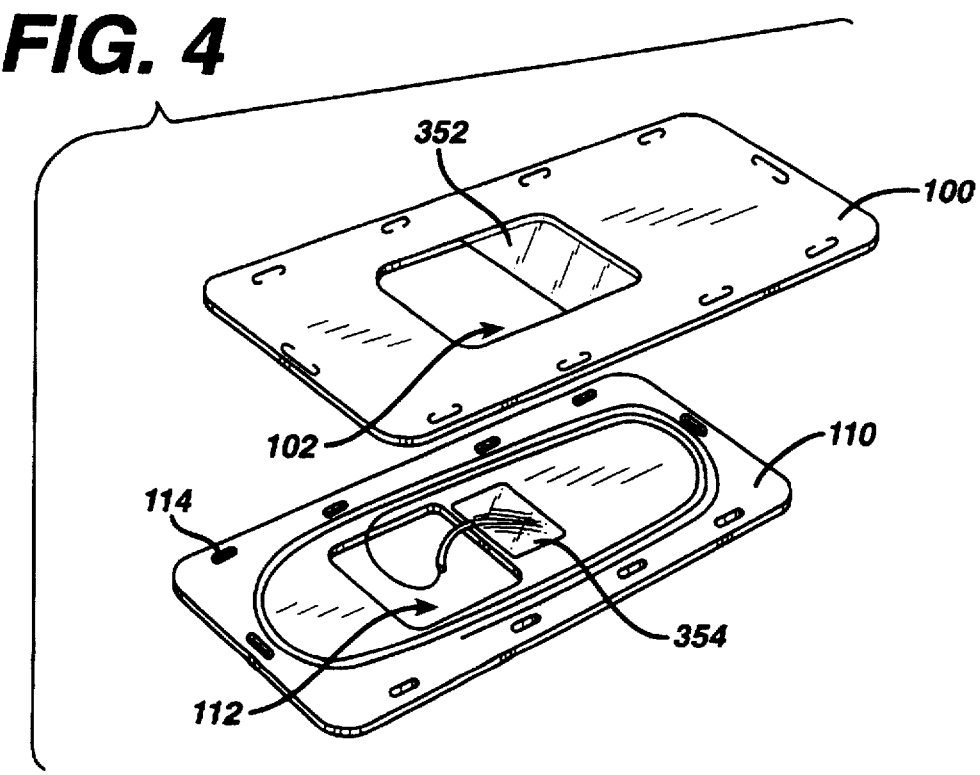
FIG. 4 is an exploded perspective view, also similar to FIG. 1, of another alternate embodiment of the present invention.

Another alternate embodiment of the present invention is illustrated in FIG. 4. In this embodiment, a variation of the "sandwich" needle park is used. The top panel 100 again has a larger central opening 102 and a top portion of the needle park 352 is disposed across a portion of the opening 102. A lower portion of the needle park 354 is disposed adjacent the central opening 112 in the lower panel 110. The lower portion 354 is preferably constructed in a manner similar to that described above with reference to FIG. 1 and is essentially a pocket in which the needle 52 resides. Preferably, both portions of the needle park 352, 354 are comprised of a clear plastic film such as Mylar®. In this embodiment, the lower portion 354 retains the needle during initial handling and during preliminary assembly steps. When the dispenser is fully assembled, the upper portion 352 reinforces the needle park area, but when a clear material is used, the entire needle 52 remains visible from at least one side of the dispenser.

Figure 5A:
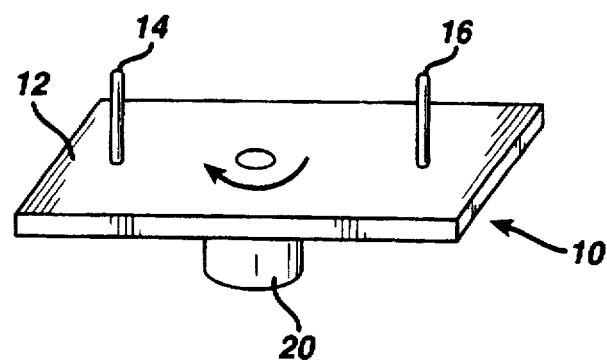
FIGS. 5A–5D are a series of perspective views illustrating the steps of winding an armed suture into a dispenser made in accordance with the present invention.
Figure 5B:
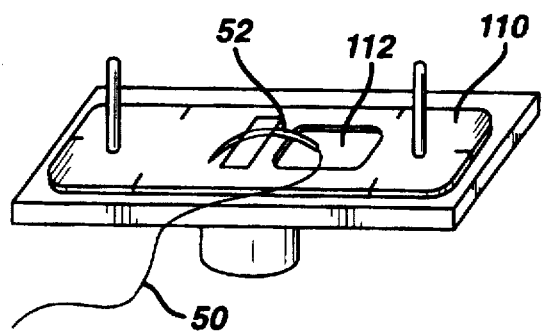
Figure 5C:
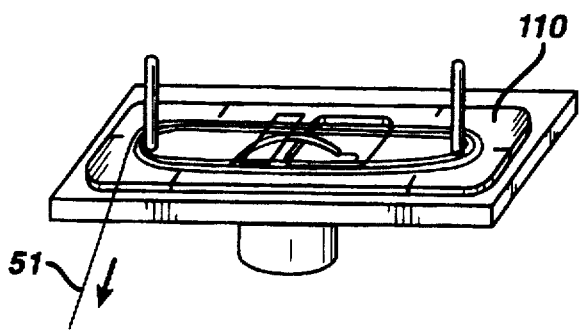
Figure 5D:
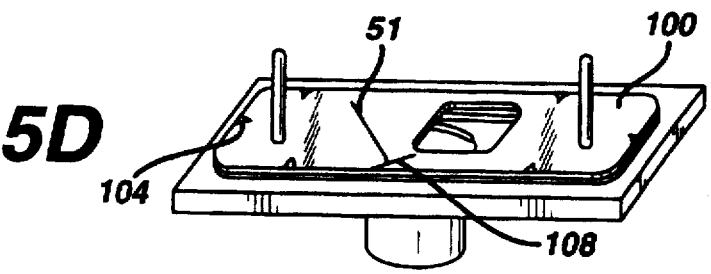

In any of the foregoing embodiments, one advantage of the dispensers of the present invention is that they may be efficiently filled in an automated or semi-automated manner in accordance with another aspect of the present invention. FIGS. 5A–5D illustrate some of the fixtures and related equipment used to carry out the sequence of filling and finishing a dispenser made in accordance with one embodiment of the methods of the present invention. FIG. 5A illustrates a perspective view of a fixture 10 that comprises a base plate 12 and several upstanding winding pins 14. The fixture 10 is preferably attached to a rotatable shaft 20. As shown in FIG. 5B, the bottom panel 110 of a dispenser is paced on the winding pins 14 and the needle 52 of an armed suture 50 is parked or otherwise retained at or around the central opening 112. The suture material is then wound in the manner shown in FIG. 5C. The proximal end or "tail" of the suture material 51 is held with downward pressure and the rotatable shaft 20 is turned so that the suture material is formed into a flat coil on the inside surface of the lower panel 110. After winding is complete, as shown in FIG. 5D, the top panel 100 is placed over the pins. At this point, the edge locks 104, 114 are engaged using an appropriate tool and the proximal end of the suture 51 is pulled through a slit 108 preferably formed in the top panel 100 to retain it in place, as shown.

Figure 6A:
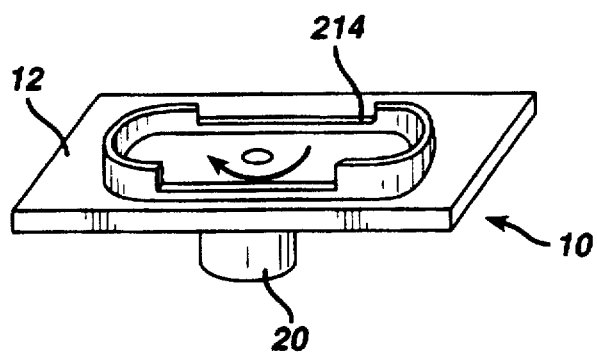
FIGS. 6A–6D are a series of perspective views similar to FIGS. 5A–5D illustrating another preferred method of winding suture material in accordance with the present invention.
Figure 6B:
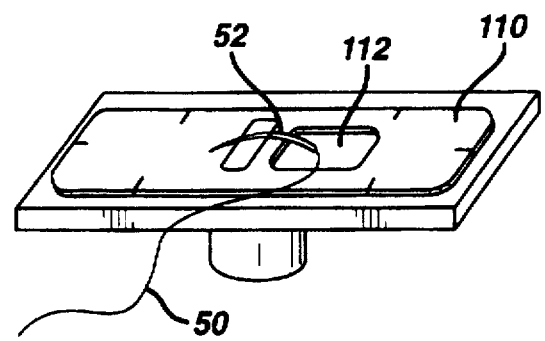
Figure 6C:
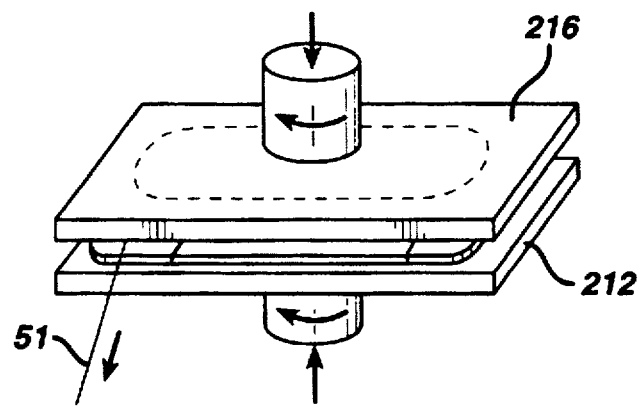
Figure 6D:
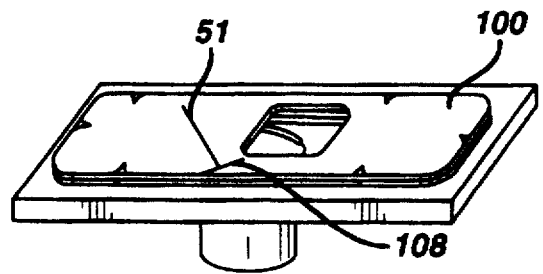

Another embodiment of the methods of the present invention is illustrated in FIGS. 6A–6D. As mentioned above, it is not always necessary to provide alignment pins or similar structures that form a central core around which the suture material is wound. Thus, referring first to FIG. 6A, it can be seen that in this embodiment, a fixture comprising a base plate 212 with a central pressure pad 214 is provided. The central pressure pad 214 may be of the raised design shown or may be of a different geometry or formed as several smaller sections. As seen in FIG. 6B, the process of loading a first panel 110 is similar to that described above with reference to FIG. 5B, except there are no pins to provide registry. As seen in FIG. 6C a second base plate 216 is placed atop the panels 100, 110 with the needle and suture disposed therebetween. The second plate 216 also most preferably includes a pressure pad, as described above. The distal end 51 of the suture is again held in pension and compressive pressure is applied to force the plates 212, 216 together. The compressed fixture is then rotated while the suture material is held in tension, resulting in a spiral wound package. As seen in FIG. 6D, the package is again completed by retaining the proximal tip 51 of the suture material using for example, a slit 108, and locking the edges of the package as necessary.

Thus, the dispenser of the present invention also provides methods for filling a suture dispenser wherein the suture material is stored in a flat spiral. The advantage of this feature is that since the needle is held in a central dispensing opening, twisting, kinking, knotting or tangling of the suture material is during withdrawal is precluded.

Figure 7A:
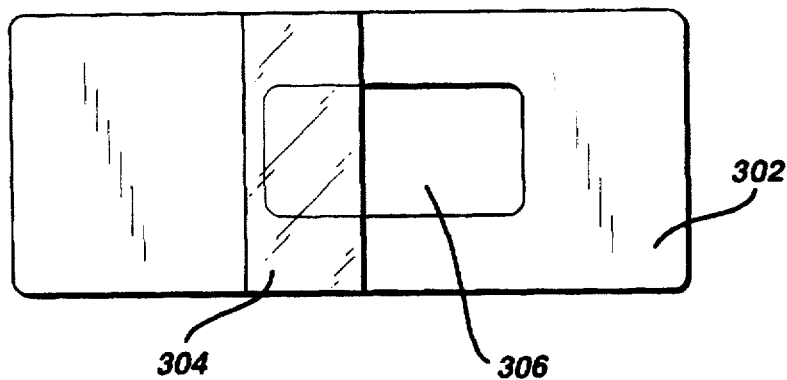
FIGS. 7A–7D illustrate an alternate embodiment of a suture dispenser.
Figure 7B:
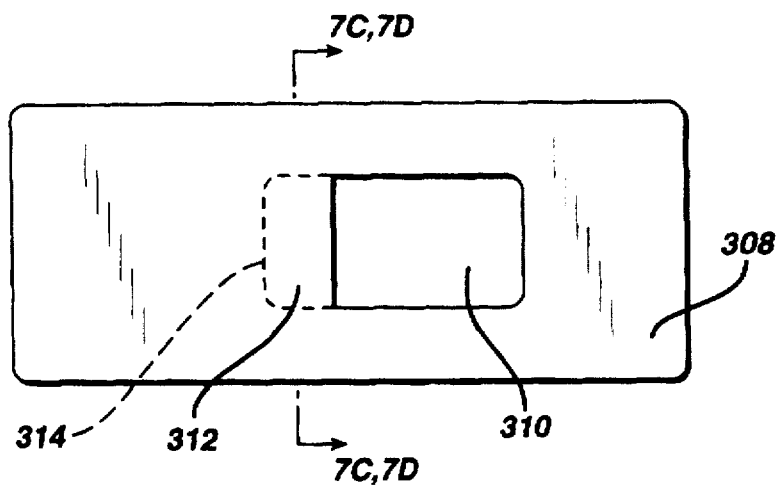

Referring now to FIGS. 7A–7D, there is shown another embodiment of a suture dispenser 300 that is also useful with the above-described winding methods. FIG. 7A is a plan view of a top panel 302 that comprises the label side component of the dispenser 300. A clear plastic window 304 is stretched across a central opening 306 in the panel. The top panel 302 cooperates with a bottom panel 308 shown in FIG. 7B. The bottom panel 308 also has a central opening 310, and a paper tab 312 is cut in the panel as an extension of the opening. The central opening 306 in the top panel is generally at least partially in registration with the paper tab 312, although most preferably both central openings 306, 310 will be in registration upon assembly.

To form a suture dispenser, the two panels 302, 308 are brought together and a needle is disposed between the plastic window 304 and the paper tab 312. Until this step of assembly, the paper tab 312 has been held in place by tie points 314 that comprise uncut sections connecting the paper tab 312 to the bottom panel 308. These tie points 314 are now broken, the paper tab 310 is urged into the plastic window 304 and heat sealed to form a needle park.

Figure 7C:
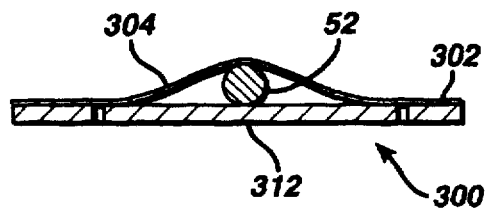
Figure 7D:
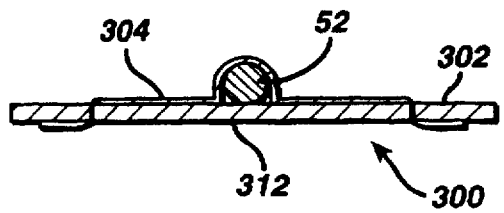

As seen in cross-section in FIG. 7C, if the clear window 304 is on the outside (label side) of the top panel 302, the paper tab 312 is heat sealed along its edges. Alternatively, if the clear window 304 is disposed on the inside surface of the top panels, as seen in FIG. 7D, the paper tab 312 actually pushes the film between its edges and the edges of the central opening 306 in the top panel 302. In either embodiment, however, the needle 52 is held by pressure underneath the clear window film 304 as shown. As mentioned above, the degree with which the clear window film conforms to the needle can be determined by the selection of the film material. As known in the art, certain thermosetting films shrink to create a taut surface, while other films form a surface that shrinks and also conforms to the surface it overlies. This embodiment of the present invention can be used with either type of thermosetting film, although film that conforms to the needle ("skin wrap") is preferred.

The advantages of this form of dispenser are that the clear window 304 is applied to the top panel 302, which is normally comprised of paper, prior to any winding operations. The paper tab 312 is formed of the material of the bottom panel, which is typically more rigid. As a result, only two components need to be handled at a winding station, and the winding operation is thus more efficient.

Although certain embodiments of the present invention have been illustrated and described in detail, these embodiments are meant to illustrate the invention and are not exhaustive. Those of skill in the art, upon review of the foregoing specification, will realize that a number of alternate embodiments, variations or modification of the methods and apparatus disclosed are readily made that do not depart from the general principles of the invention. Accordingly, reference should be had to the appended claims in order to determine the full scope of the present invention.

What is claimed is:

1. A dispenser for sutures comprising:
   a first, individual, separate, substantially flat panel comprising a central opening and edge locks, said panel having a top and a bottom;
   a second, individual, separate, substantially flat panel comprising a central opening and edge locks, said second panel having a top and bottom wherein said first panel is mounted to said second panel such that the bottom of the first panel is adjacent to the top of the second panel; and
   a needle park disposed adjacent the central opening of one of the first and second panels, wherein the edge locks cooperate to retain the first panel against the second panel.

2. The dispenser of claim 1, wherein the needle park comprises at least one strip of material disposed adjacent the central opening of at least one of the first and second panels.

3. The dispenser of claim 2, wherein the strip of material comprises a transparent material.

4. The dispenser of claim 2, wherein the strip of material further comprises a surface covered with an adhesive material.

5. The dispenser of claim 2, wherein the strip of material further comprises a surface covered with a cohesive material.

6. The dispenser of claim 2, wherein the strip of material further comprises a surface covered with a thermoformable material.

7. The dispenser of claim 2, wherein the strip of material further comprises a surface covered with a heat shrink material.

8. The dispenser of claim 2 comprising a first strip of material disposed adjacent the central opening of the first panel and a second strip of material disposed adjacent the central opening of the second panel.

9. The dispenser of claim 1 wherein the central opening of the first panel is a different size than the central opening in the second panel, whereby when the panels are placed in registration, a portion of one of the panels overlies at least part of one of the central openings.

10. The dispenser of claim 1 wherein the central opening of the first panel is disposed in a different location than the central opening in the second panel, whereby when the panels are placed in registration, a portion of one of the panels overlies at least part of one of the central openings.

11. The dispenser of claim 1, wherein the needle park comprises at least one retainer molded directly on to at least one of the first and second panels.

12. The dispenser of claim 11, wherein the retainer comprises a block for restraining a distal tip of a needle.

13. The dispenser of claim 11 wherein the retainer comprises a first resilient member and a second member adjacent thereto, wherein the needle is provided with a friction fit between the first and second member.

14. A needle and suture contained in a dispenser comprising:
- a first, individual, separate, substantially flat panel comprising a central opening and edge locks, said panel having a top and a bottom;
- a second, individual, separate, substantially flat panel comprising a central opening and edge locks, said second panel having a top and a bottom, wherein said first panel is mounted to said second panel such that the bottom of the first panel is adjacent to the top of the second panel; and,
- a needle park disposed adjacent the central opening of one of the first and second panels, wherein the edge locks on the first and second panels cooperate to retain the first panel against the second panel.

15. The needle and suture contained in a dispenser of claim 14, wherein the first panel comprises a central opening partially covered by a layer of plastic film; and the second panel comprises a paper tab, wherein the paper tab is detached from the second panel and heat sealed against the plastic film to form a needle park.

* * * * *